United States Patent [19]

Regelman

[11] Patent Number: 4,719,245

[45] Date of Patent: Jan. 12, 1988

[54] FLEXIBLE POLYISOCYANURATE-URETHANE FOAM

[75] Inventor: Dale F. Regelman, Wallingford, Conn.

[73] Assignee: The Dow Chemical Company, Midland, Mich.

[21] Appl. No.: 909,546

[22] Filed: Sep. 22, 1986

Related U.S. Application Data

[62] Division of Ser. No. 737,837, May 28, 1985, Pat. No. 4,632,989, which is a division of Ser. No. 587,429, Mar. 8, 1984, Pat. No. 4,536,490.

[51] Int. Cl.$^4$ ............................................. C08J 9/00
[52] U.S. Cl. .................................. 521/128; 521/131; 521/902
[58] Field of Search ........................ 521/902, 128, 131

[56] References Cited

U.S. PATENT DOCUMENTS

| | | | |
|---|---|---|---|
| 3,330,828 | 7/1967 | Grogler et al. | 528/44 |
| 4,011,180 | 3/1977 | Lockwood et al. | 521/902 |
| 4,025,469 | 5/1977 | Kauffman | 521/902 |
| 4,036,792 | 7/1977 | Hopkins, Jr. | 521/902 |
| 4,101,465 | 7/1978 | Lockwood et al. | 521/902 |
| 4,111,914 | 9/1978 | Kresta et al. | 528/48 |
| 4,235,976 | 11/1980 | Haas et al. | 521/902 |
| 4,326,043 | 4/1982 | Narayan et al. | 521/902 |
| 4,359,541 | 11/1982 | Patton, Jr. et al. | 521/902 |
| 4,359,550 | 11/1982 | Narayan et al. | 521/902 |
| 4,382,125 | 5/1983 | Narayan et al. | 521/902 |
| 4,410,641 | 10/1983 | Narayan et al. | 521/902 |
| 4,412,073 | 12/1986 | Robin | 521/902 |
| 4,514,525 | 4/1985 | Ashida et al. | 521/902 |
| 4,555,418 | 11/1985 | Snider et al. | 521/902 |

OTHER PUBLICATIONS

Gompper et al., Angewandte Chemie, Int. Ed., 6, 453 (1967).

Primary Examiner—Morton Foelak
Attorney, Agent, or Firm—J. S. Rose

[57] ABSTRACT

Disclosed are novel compositions capable of catalytically trimerizing organic isocyanates said compositions comprising solutions of the reaction products obtained by reacting in an inert solvent in substantially equimolar proportions electron-rich ketene-aminals with electron-poor olefins having the respective formulae (I) and (II)

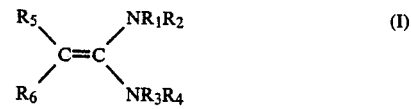

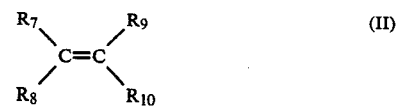

The variously substituted electron-rich ketene-aminals (I), as the name implies, have high electron density associated with the double bond because of the two tertiary amine groups while the electron-poor olefins (II) have the opposite situation due to the presence of electron withdrawing substituents $R_9$ and $R_{10}$.

Also discosed is an improved process for trimerizing organic isocyanates using the above catalyst compositions including the preparation of polyisocyanurate polymers and isocyanurate-modified polyisocyanates.

5 Claims, No Drawings

FLEXIBLE POLYISOCYANURATE-URETHANE FOAM

CROSS-REFERENCE TO RELATED APPLICATION

This is a division of application Ser. No. 737,837, filed May 28, 1985, now U.S. Pat. No. 4,632,989, which is a division of application Ser. No. 587,429, filed Mar. 8, 1984, now U.S. Pat. No. 4,536,490.

BACKGROUND OF THE INVENTION

1. Field of the Invention

This invention relates to novel compositions derived from the reaction of particular ketene-animals with particular olefins and the use of said compositions as catalysts in the trimerization of organic isocyanates.

2. Description of the Prior Art

There are numerous catalysts known in the art for the trimerization of isocyanates and most of them suffer from a drawback of one sort or another. For example, in the preparation of isocyanurate-modified polyisocyanates the trimerization must be interrupted by the addition of a catalyst poison as taught in U.S. Pat. No. 3,330,828. Alternatively, in the use of self-deactivating catalysts such as the ar-sulfonium arenoxide zwitterions as taught in U.S. Pat. No. 4,111,914, the catalysts are expensive and difficult to prepare. Also, the prior art catalysts often result in highly colored products which are not stable upon storage and some products even emit odors due to the catalyst.

In regard to the complete trimerization of isocyanates using prior art catalysts, one of the problems has been the achievement of good conversion to polyisocyanurate once the polymer has gelled. Concurrently, once the polymer has solidified the catalyst cannot be removed and the majority of prior art catalysts have an adverse effect on polymer properties over prolonged periods.

I have now discovered what I believe to be novel compositions which act as catalysts in trimerizing organic isocyanates. The catalysts in accordance with the present invention overcome the drawbacks of the prior art catalysts noted above and their advantageous features will be discussed in detail below.

SUMMARY OF THE INVENTION

This invention comprises compositions capable of catalytically trimerizing an organic isocyanate said compositions comprising a solution of the product obtained by reacting in an inert solvent in substantially equimolar proportions a ketene-animal and an olefin having the respective formulae (I) and (II)

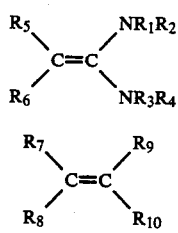

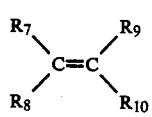

wherein $R_1$, $R_2$, $R_3$, and $R_4$ when taken separately are independently selected from the group consisting of lower-alkyl, aralkyl, cycloalkyl, and, when taken together as $R_1$ with $R_2$ and $R_3$ with $R_4$ with the respective nitrogen atoms to which they are attached represent independently heterocyclic groups having 6 or 7 ring atoms, $R_5$ and $R_6$ are independently selected from the group consisting of hydrogen, lower-alkyl, aryl, aralkyl, and cycloalkyl, $R_7$ and $R_8$ when taken separately are independently selected from the group consisting of hydrogen, lower-alkyl, aryl, aralkyl, and cycloalkyl, provided that $R_7$ and $R_8$ are not both hydrogen at the same time, and, $R_7$ and $R_8$, when taken together with the carbon atom to which they are attached represent a cyclic hydrocarbon group having 5 or 6 carbon atoms in the ring, and $R_9$ and $R_{10}$ represent the same or different electron withdrawing groups.

This invention also comprises improved methods for the trimerization of organic isocyanates comprising the use of the above compositions as trimerization catalysts.

The term "lower-alkyl" means alkyl having from 1 to 8 carbon atoms, inclusive, such as methyl, ethyl, propyl, butyl, pentyl, hexyl, heptyl, octyl, and isomeric forms thereof.

The term "aralkyl" means the monovalent radical obtained by removing one hydrogen atom from the alkyl portion of an aromatic alkane hydrocarbon having 7 to 18 carbon atoms. Illustrative of aralkyl are benzyl, phenethyl, phenylpropyl, benzhydryl, naphthylmethyl, and the like.

The term "cycloalkyl" means cycloalkyl having 4 to 6 ring carbon atoms, inclusive, such as cyclobutyl, cyclopentyl, cyclohexyl, and the like.

The term "heterocyclic groups having 6 or 7 ring atoms" means a heterocyclic radical containing at least the basic valence ring nitrogen and optionally containing one or more additional hetero atoms such as nitrogen, oxygen, and sulfur. Illustrative of such groups are N-piperidinyl, N-(4-methylpiperidinyl), N-morpholinyl, N-(4-methylpiperazinyl), N-(4-ethylpiperazinyl), N-hexahydroxazepinyl, and the like.

The term "aryl" means the radical obtained by removing one nuclear hydrogen atom from an aromatic hydrocarbon having from 6 to 12 carbon atoms, inclusive. Illustrative of aryl are phenyl, tolyl, naphthyl, biphenylyl, and the like.

The term "cyclic hydrocarbon group having 5 or 6 carbon atoms in the ring" is inclusive of cyclopentylidene, cyclopentenylidene, cyclopentadienylidene, cyclohexylidene, cyclohexenylidene, cyclohexadienylidene, and the like, and the corresponding cyclic hydrocarbons having substituents such as alkyl groups and hydrocarbon rings fused thereon to for radicals such as indenylidene, isoindenylidene, fluorenylidene, and the like.

The term "electron withdrawing group" means a group capable of attracting electrons and is inclusive of groups having the formulae $-CN$, $-COR_{11}$, $COOR_{11}$, $CONH_2$, $-CHO$, $-NO_2$, $-SO_2R_{11}$, and $-SOR_{11}$ wherein $R_{11}$ represents lower-alkyl, aralkyl, aryl, and cycloalkyl as defined above.

DETAILED DESCRIPTION OF THE INVENTION

While not wishing the present invention to be bound by any theoretical considerations but only by the claims appended hereinbelow, it is believed the novel compositions in accordance with the present invention are complex mixtures. At any given time, the solutions are believed to comprise reversible equilibrium mixtures of such components as, inter alia, 1,4-dipolar compounds having the formula (III) below and the fully cyclized derivatives thereof (IIIa), and 1:2 and 2:1 cyclo adducts of the type (IV) and (V), respectively, derived from the reaction of (III) with excess (I) and (II), respectively, and other possible complex ion-pair components all dissolved in the solvent.

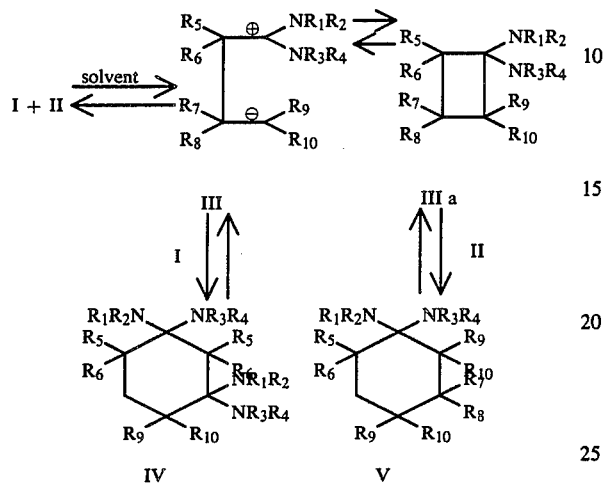

Gompper et al., Angewandte Chemie, Int. Ed., 6, 453 (1967) have postulated the formation of 1:1 and 1:2 or 2:1 cyclo adducts and the isolation of 1,4-dipolar compounds from the reaction of electron-rich olefins with electron-poor olefins which are related to, but differently substituted from, the olefins (I) and (II) above.

A carbon 13 nuclear magnetic resonance spectrum of a typical composition in accordance with the present invention is very complex containing as many as 84 resonance peaks. Comparatively, the predicted number of resonance peaks for a single component such as the 1,4-dipolar compound (III) would be about 14.

When the solvent is removed from the present compositions the residue is no longer active as an isocyanate trimerization catalyst.

The present compositions are very easily prepared simply by thoroughly mixing the ketene-aminal with the olefin in substantially equimolar proportions in an inert solvent, optionally under an inert atmosphere such as nitrogen or argon. The term "inert solvent" means any solvent which does not react with either (I) or (II) or otherwise interfere with the formation of the compositions.

Generally speaking, with the more reactive ketene-aminals ($R_5$ and $R_6$ both hydrogen) the reaction is essentially immediate at ambient room temperature (about 20° C.) as evidenced by the immediate formation of a deeply colored solution (e.g. yellow to red) upon mixing the reactants.

That the reaction is essentially immediate is evidenced by the infrared absorption spectrum of a sample of the reaction solution within minutes after mixing the reactants (see Example 6 below). The absorptions due to the double bonds at about 1645 cm$^{-1}$ (ketene-aminal) and 2222 cm$^{-1}$, 1600 cm$^{-1}$ (olefin II) have completely disappeared.

In the case of the substituted ketene-aminals ($R_5$ and $R_6$ having the various substituents set forth above) the reaction does not proceed as fast.

The order of mixing is not critical, that is to say, either reactant can be predissolved in the solvent with the subsequent addition of the remaining reactant. Alternatively, the reactants can be mixed followed by the addition of the solvent.

Advantageously, the solvents are polar aromatic solvents such as nitrobenzene, dichlorobenzene, toluene, xylene, and the like; halogenated aliphatic solvents such as chloroform, carbon tetrachloride, tetrachloroethane, and the like; dipolar aprotic solvents such as acetonitrile, formamide, dimethylformamide, diethylformamide, dimethylacetamide, dimethylsulfoxide, tetramethylsulfone, hexamethylphosphoramide, tetramethyl urea, and the like; alcohols such as methanol, ethanol, isopropanol, cyclohexanol, and the like; organic polyols having at least two hydroxyl groups and inclusive of organic polyols having a MW from about 60 to about 4000 such as ethylene glycol, diethylene glycol, propylene glycol, dipropylene glycol, liquid polyethyleneoxy glycols, liquid polyoxypropylenepolyoxyethylene glycols, and the like.

Preferred classes of solvents are the dipolar aprotic solvents and the organic polyols with the latter class being the most preferred.

The concentration of reactants employed in the solvent is not in any way critical. Advantageously, the combined weight of (I) and (II) is from about 5 to about 95 percent by weight in the solvent, preferably from about 15 to 75 percent by weight. Accordingly, the concentrations of the reaction product mixtures in the final compositions are the same as the above ranges.

The ketene-aminals are well known compounds which are readily obtainable by known synthetic methods. Typically, they can be prepared by the reaction of an excess of the appropriate secondary amine or mixture of secondary amines with ethoxyacetylene according to the procedure of D. H. Clemens et al., J. Org. Chem, 29, 2932 (1964).

Illustrative but not limiting, of the ketene-aminals are 1,1-bis(dimethylamino)ethylene, 1,1-bis(dimethylamino)-2-methylethylene, 1,1-bis(dimethylamino)-2,2-dimethylethylene, 1,1-bis(dimethylamino)-2,2-diethylethylene, 1,1-bis(dimethylamino)-2,2-dibutylethylene, 1,1-bis(dimethylamino)-2-phenylethylene, 1,1-bis(diethylamino)ethylene, 1,1-bis(diethylamino)-2-methylethylene, 1,1-bis(dipropylamino)ethylene, 1,1-bis(dibutylamino)ethylene, 1,1-bis(dibutylamino)-2-methylethylene, 1,1-bis(dibutylamino)-2-benzylethylene, 1,1-bis(dibutylamino)-2-cyclohexylethylene, 1,1-bis(dipentylamino)ethylene, 1,1-bis(dihexylamino)ethylene, 1,1-bis(dihexylamino)-2-methylethylene, 1,1-bis(diheptylamino)ethylene, 1,1-bis(dioctylamino)ethylene, 1,1-bis(dioctylamino)-2-methylethylene, 1,1-bis(methylethylamino)ethylene, 1,1-bis(dibenzylamino)ethylene, 1,1-bis(dibenzylamino)-2-methylethylene, 1,1-bis(dicyclopentylamino)ethylene, 1,1-bis(dicyclohexylamino)ethylene, 1,1-bis(dicyclohexylamino)-2-methylethylene, 1,1-bis(N-piperidinyl)ethylene, 1,1-bis(N-piperidiny)-2-methylethylene, 1,1-bis(N-4-methylpiperidinyl)ethylene, 1,1-bis(N-morpholinyl)ethylene, 1,1-bis(N-morpholinyl)-2-methylethylene, 1,1-bis(N-piperazinyl)ethylene, 1,1-bis(N-piperazinyl)-2-methylethylene, 1,1-bis(N-hexahydroazepinyl)ethylene, 1,1-bis(N-piperidinyl)-2,2-dimethylethylene, and the like.

In the case of the olefins (II) they are, for the most part, commercially available. Alternatively, they are readily prepared using the aldol type condensation reaction between the appropriately substituted aldehyde or ketone with, for example, a malononitrile, a dialkylmalonate, acetylacetone, dinitromethane, and the like.

The $R_7$ and $R_8$ radicals can represent a wide variety of substituents as defined above but, in order to avoid objectionable polymer formation, should not be both hydrogen at the same time.

Illustrative of the electron withdrawing groups $R_9$ and $R_{10}$ are cyano, acetyl, propionyl, butyryl, phenylacetyl, benzoyl, cyclopentanoyl, cyclohexanoyl, carbomethoxy, carboethoxy, carbamoyl, formyl, nitro, methylsulfonyl, ethylsulfonyl, butylsulfonyl, phenylsulfonyl, cyclohexylsulfonyl, methylsulfinyl, ethylsulfinyl, phenylsulfinyl, and the like.

Preferred of the electron withdrawing groups are cyano, acetyl, propionyl, carbomethoxy, and carboethoxy.

Illustrative, but not limiting, of the olefins are 1,1-dicyano-2-methylethylene(ethylidene malononitrile), 1,1-dicyano-2-ethylethylene, 1,1-dicyano-2-propylethylene, 1,1-dicyano-2-butylethylene, 1,1-dicyano-2-pentylethylene, 1,1-dicyano-2-hexylethylene, 1,1-dicyano-2-heptylethylene, 1,1-dicyano-2-octylethylene, 1,1-dicyano-2-phenylethylene(benzylidene malononitrile), 1,1-dicyano-2-(p-tolyl)ethylene, 1,1-dicyano-2-benzylethylene, 1,1-dicyano-2-cyclohexylethylene, 1,1-dicyano-2,2-dimethylethylene, 1,1-dicyano-2,2-diphenylethylene, 1,1-bis-acetyl-2-methylethylene, 1,1-bisacetyl-2-phenylethylene, 1,1-bispropionyl-2-phenylethylene, 1,1-bisbutyryl-2-phenylethylene, 1,1-bisbenzoyl-2-phenylethylene, 1,1-bis-carbethoxy-2-phenylethylene(diethyl benzylidenemalonate), 1,1-bis-carbethoxy-2-methylethylene(diethyl ethylidenemalonate), 1,1-biscarbethoxy-2,2-dimethylethylene(diethyl isopropylidenemalonate), 1,1-dicyano-2,2-(tetramethylene)ethylene, 1,1-dicyano-2,2-(pentamethylene)ethylene, 1,1-dicyano-2,2-fluorenylideneethylene(fluorenylidene malononitrile), 1,1-dicyano-2,2-(4,5,7-trinitrofluorenylidene)ethylene(4,5,7-trinitrofluorenylidene malononitrile), 1-nitro-1-carbethoxy-2-phenylethylene, 1-cyano-1-carbethoxy-2-phenylethylene, and the like.

It is to be understood that any of the ketene-aminals set forth above can be reacted with any one of the olefins also set forth above to form compositions in accordance with the present invention.

The compositions described above can be used as catalysts for the preparation of a broad variety of products arising from the polymerization of isocyanates including solid polymers such as solid and micro-cellular elastomers, RIM elastomers, and the like; isocyanurate containing polyisocyanate prepolymers; and cellular polymers when reacted under foam forming conditions Typical procedures and ingredients which can be used in combination with the catalyst solutions for the preparation of polyisocyanurate solids, foams, and prepolymers are set forth in U.S. Pat. Nos. 3,711,444; 3,896,052; 3,903,018 and 4,111,914 whose disclosures relative thereto are hereby incorporated herein by reference.

Advantageously, the catalyst solution is employed in such an amount that the total solids content of the solution, expressed by the combined weight of (I) and (II), falls within a range of from about 0.5 to about 10.0 parts, preferably from about 0.8 to about 5.0 parts per mole of isocyanate being polymerized.

Preferred catalyst solutions are those wherein the solvent is a dipolar aprotic solvent or an organic polyol as defined above. Most preferred are the organic polyols.

While any of the ketene-aminals and olefins defined above can be reacted together to form the catalyst solutions in accordance with the present invention preferred classes of the above reactants and preferred species thereunder are as follows.

I. KETENE-AMINALS $R_1$ with $R_2$ and $R_3$ with $R_4$ taken together with their respective nitrogen atoms to form the same heterocyclic groups defined above or $R_1$, $R_2$, $R_3$, and $R_4$ are all the same lower-alkyl groups with the $R_5$ and $R_6$ substituents falling in one of the following three categories.

(a) $R_5$ and $R_6$ are both hydrogen,
1,1-bis(dimethylamino)ethylene,
1,1-bis(diethylamino)ethylene,
1,1-bis(dipropylamino)ethylene,
1,1-bis(dibutylamino)ethylene,
1,1-bis(N-piperidinyl)ethylene,
1,1-bis(N-morpholinyl)ethylene, and
1,1-bis(N-piperazinyl)ethylene;

(b) $R_5$ and $R_6$ are both lower-alkyl:
1,1-bis(dimethylamino)-2,2-dimethylethylene,
1,1-bis(diethylamino)-2,2-dimethylethylene,
1,1-bis(dipropylamino)-2,2-dimethylethylene,
1,1-bis(dibutylamino)-2,2-dimethylethylene,
1,1-bis(N-piperidinyl)-2,2-dimethylethylene, and
1,1-bis(N-morpholinyl)-2,2-dimethylethylene;

(c) $R_5$ and $R_6$ are hydrogen and lower-alkyl respectively:
1,1-bis(dimethylamino)-2-methylethylene,
1,1-bis(diethylamino)-2-methylethylene,
1,1-bis(dipropylamino)-2-methylethylene,
1,1-bis(dibutylamino)-2-methylethylene,
1,1-bis(N-piperidinyl)-2-methylethylene, and
1,1-bis(N-morpholinyl)-2-methylethylene; and the like.

II. OLEFINS $R_7$ and $R_8$ are hydrogen and aryl respectively and $R_9$ and $R_{10}$ are both the same electron withdrawing group, the latter being the preferred electron withdrawing groups set forth above:
1,1-dicyano-2-phenylethylene,
1,1-dicyano-2-(p-tolyl)ethylene,
1,1-dicyano-2[p-(N-morpholinyl)phenyl]ethylene,
1,1-bisacetyl-2-phenylethylene,
1,1-bispropionyl-2-phenylethylene,
1,1-biscarbomethoxy-2-phenylethylene,
1,1-biscarboethoxy-2-phenylethylene, and the like.

It is to be understood that any one of the preferred ketene-aminals can be reacted with any one of the preferred olefins to form preferred compositions in accordance with the present invention.

An advantageous feature of the present catalyst compositions is their ability to initiate isocyanate trimerization at room temperature (about 20° C.).

Surprisingly, the choice of ketene-aminal type plays an unexpected role in the course of the trimerization process. Those compositions arising from the ketene-aminals in the (Ia) class set forth above (i.e. $R_5$ and $R_6$ both hydrogen) are not stable for long periods of time, and preferably, are used within about 5 to 10 minutes after their preparation. These catalysts deactivate with time and particularly at elevated temperatures. Accordingly, the catalysts falling within this class are particularly useful for the preparation of polyisocyanate prepolymers containing isocyanurate linkages. Infrared absorption spectra of these products show the presence of both the isocyanurate and isocyanate groups and the intensities of the groups varying with the extent to which the trimerization process is carried out.

A particularly advantageous and unexpected feature of the (Ia) type catalysts is the control which they can provide over the conversion of isocyanate to isocyanurate. Generally speaking, the addition of small portions of a specific amount of catalyst over a period of time will result in greater catalyst efficiency (greater conversion to trimer) compared to the same specific amount added all at once.

Those compositions arising from the (Ib) (i.e. $R_5$ and $R_6$ both lower-alkyl) and (Ic) (i.e. $R_5$=hydrogen and $R_6$=lower-alkyl) classes of ketene-aminals set forth above, in contrast to the (Ia) class, are completely stable over prolonged periods of storage.

The (Ib) class provides catalyst compositions characterized by lower catalytic activity than those from the (Ic) class. Accordingly, the former are advantageously employed in the preparation of polyisocyanate prepolymers containing isocyanurate linkages while the latter are preferred when fully trimerized polymers are desired. Infrared spectra of the fully trimerized products show the characteristic strong absorptions at 1710 cm$^{-1}$ and 1410 cm$^{-1}$ for polyisocyanurate polymers.

The (Ic) based catalysts possess some highly unexpected but most useful properties when it comes to trimerizing isocyanates. For example, because of their high catalyst activity, they can be employed in the preparation of molded polyisocyanurate parts without the need for applying external heat to the molds, particularly in thin mold sections.

Further, depending on the concentration of catalyst employed, the (Ic) based catalyst compositions starting at about room temperature (20° C.) can be used to convert a polyisocyanate either very rapidly or very slowly to the polyisocyanurate product.

The isocyanates which can be polymerized in accordance with the present invention can be any of the organic isocyanates, particularly organic polyisocyanates known to those skilled in the art which are referred to in the patents cited supra.

Typical, but not limiting, of the isocyanates which can be used are phenyl isocyanate, hexamethylene diisocyanate, 4,4'-methylenebis(phenyl isocyanate), m- and p-phenylene diisocyanate, 2,4- and 2,6-toluene diisocyanate and mixtures of the 2,4- and 2,6-isomers, polymethylenepolyphenyl polyisocyanates, the various types of liquefied methylenebis(phenyl isocyanates) obtained by reacting the methylenebis(phenyl isocyanate) in varying proportions with minor amounts of one or more glycols and the liquid diisocyanates comprising the carbodiimide-containing methylenebis(phenyl isocyanates) having an isocyanate equivalent weight of from about 130 to about 180. Also included within the scope of the present invention are isocyanate terminated polyurethane prepolymers.

Preferred amongst the typical species cited above are the aromatic polyisocyanates and hexamethylene diisocyanate.

Preferred aliphatic and aromatic polyisocyanate prepolymers containing isocyanurate linkages are those prepolymers prepared from hexamethylene diisocyanate and the liquid carbodiimide-containing methylenebis(phenyl isocyanates) described above. Preferred isocyanate equivalent weight ranges for these prepolymers are from about 90 to about 250 and from about 160 to about 250 respectively.

The various products described above which are derived by the isocyanate polymerization methods in accordance with the present invention can be used in a variety of applications. For instance, solid molded parts derived from these polymers are useful in the production of auto parts such as body elements, panels, doors, engine hoods, and the like. Cellular products both flexible and rigid derived from these polymers, by virtue of their high temperature resistance qualities, can be used as thermal barriers and insulation materials for high temperature pipe lines, ovens, storage tanks, and in the production of flame retardant laminates and flame retardant seat cushions and the like.

The following examples describe the manner and process of making and using the invention and set forth the best mode contemplated by the inventor of carrying out the invention but are not to be construed as limiting.

EXAMPLES 1–15

A small (2 oz.) wide mouth sample bottle was charged with 1.22 g. (0.0065 mole) of 1,1-bisacetyl-2-phenylethylene (prepared from benzaldehyde and acetylacetone) dissolved in about 4 g. of vacuum dried Poly-G 55-112 (a 1000 MW polyoxyethylenepolyoxypropylene diol having an EO content of about 50 percent supplied by Olin Chemicals, New Haven, Conn.). The solution was stirred with a magnet stirrer at ambient temperature (about 20° C.) and over a 10 second period 1.42 g. of 89 percent pure 1,1-bis(N-piperidinyl)ethylene (i.e. 1.26 g., 0.0065 mole of pure material) was added dropwise causing an immediate exotherm to about 35° C. A deep yellow solution formed which was stirred for an additional 10 seconds and then the sample bottle was capped for storage of the solution until used as a trimerization catalyst.

Thus there was obtained a composition in accordance with the present invention wherein the solids content of the reaction product in the Poly-G 55-112 was about 38 percent by weight.

Using a similar procedure as above and the ketene-aminals, olefins, and solvents set forth in Table I there were prepared four compositions in accordance with the present invention identified as Examples 2 to 5, inclusive, in Table I.

TABLE I

| | ketene-aminal (moles) | olefin (moles) | solvent (% conc. product) |
|---|---|---|---|
| Ex. 2 | 1,1-bis(N—morpholinyl)-ethylene (0.00065 m) | 1,1-bisacetyl-2-phenylthylene (0.0065 m) | Poly-G 55-112 (20%) |
| Ex. 3 | 1,1-bis(N—morpholinyl)-ethylene (0.0051 m) | benzylidene malononitrile (0.0051 m) | acetonitrile (36%) |
| Ex. 4 | 1,1-bis(N—morpholinyl)-ethylene (0.0025 m) | p-(N—morpholinyl)-benzylidene malononitrile | dimethylacetamide (22%) |

TABLE I-continued

| | ketene-aminal (moles) | olefin (moles) | solvent (% conc. product) |
| --- | --- | --- | --- |
| Ex. 5 | 1,1-bis(N—morpholinyl)-ethylene (0.0065 m) | (0.0025 m) diethyl benzyl-idenemalonate (0.0065 m) | Poly-G 55-112 (22.5%) | forth in Table II there were prepared eleven compositions in accordance with the present invention identified as Examples 7 to 17, inclusive, in Table II.

TABLE II

| | ketene-aminal (moles) | olefin (moles) | solvent (% conc. product) |
| --- | --- | --- | --- |
| Ex. 7 | 1,1-bis(N—piperidinyl)-2-methylethylene (0.0065 m) | diethyl benzylidene malonate | Poly-G 55-112 (22%) |
| Ex. 8[1] | 1,1-bis(N—piperidinyl)-2-methylethylene (0.0065 m) | diethyl ethylidene malonate | Poly-G 55-112 (20%) |
| Ex. 9[1] | 1,1-bis(N—piperidinyl)-2-methylethylene (0.0065 m) | 1,1-bisacetyl-2-phenylethylene (0.0065 m) | Poly-G 55-112 (20%) |
| Ex. 10[2] | 1,1-bis(N—piperidinyl)-2-methylethylene (0.0065 m) | 4,5,7-trinitrofluor-enylidene malono-nitrile (0.0065 m) | Poly-G 55-112 (26%) |
| Ex. 11 | 1,1-bis(N—piperidinyl)-2-methylethylene (0.013 m) | diethyl isopropyl-idenemalonate (0.013 m) | Poly-G 55-112 (20%) |
| Ex. 12 | 1,1-bis(N—piperidinyl)-2-methylethylene (0.0065 m) | fluorenylidene malononitrile (0.0065 m) | Poly-G 55-112 (21%) |
| Ex. 13 | 1,1-bis(N—piperidinyl)-2-methylethylene (0.0065 m) | 1-nitro-1-carb-ethoxy-2-phenyl-ethylene (0.0065 m) | Poly-G 55-112 (21%) |
| Ex. 14[3] | 1,1-bis(N—piperidinyl)-2-methylethylene (0.0065 m) | 1-cyano-1-carb-ethoxy-2-phenyl-ethylene (0.0065 m) | Poly-G 55-112 (20%) |
| Ex. 15[4] | 1,1-bis(N—morpholinyl)-2-methylethylene (0.020 m) | benzylidene malononitrile (0.020 m) | Poly-G 55-112 and chloroform (21%) |
| Ex. 16 | 1,1-bis(dibutylamino)-2-methylethylene (0.0065 m) | benzylidene malononitrile (0.0065 m) | acetonitrile (65%) |
| Ex. 17 | 1,1-bis(dimethylamino)-2-methylethylene (0.0065 m) | 1,1-bisacetyl-2-phenylethylene (0.0065 m) | Poly-G 55-112 (17%) |

Footnotes to Table II
[1] Stirred for 2.5 hours after initial mixing of reactants.
[2] Stirred for 2.0 hours after initial mixing of reactants.
[3] Stirred for 3.0 hours after initial mixing of reactants.
[4] Benzylidene malononitrile added as a chloroform solution to solution of ketene-aminal dissolved in the Poly-G 55-112.

EXAMPLES 6-17

Using the procedure set forth in Example 1, 1.0 g. (0.0065 mole) of benzylidene malononitrile was dissolved in 10 ml. of Poly-G 55-112 and there was added dropwise 1.35 g. (0.0065 mole) of 1,1-bis(N-piperidinyl)-2-methylethylene. There was an immediate formation of a pasty tan colored material which, after stirring overnight, became a deep orange solution.

An infrared spectrum of the reaction solution determined within minutes after mixing the reactants showed the complete disappearance of the double bond absorption bands at 1645 cm$^{-1}$ due to the 1,1-bis(N-piperidinyl)-2-methylethylene and at 2222 cm$^{-1}$ and 1600 cm$^{-1}$ due to the benzylidene malononitrile.

Thus there was obtained a composition in accordance with the present invention wherein the solids content of the reaction product in the Poly-G 55-112 was about 18 percent by weight.

Using a similar procedure as above (except where noted) and the ketene-aminals, olefins, and solvents set

EXAMPLE 18

This example sets forth three isocyanurate-modified polyisocyanates (samples 1, 2, and 3) prepared in accordance with the present invention using methylene-bis(-phenylisocyanates) having high ortho-para' isomer contents and which are liquids at room temperature. The ingredients and proportions in parts by weight are set forth in Table III.

The modified polyisocyanates were prepared simply by first charging the starting polyisocyanate to a reagent bottle equipped with a magnet stirring bar. Then the freshly prepared catalyst compositions in accordance with the invention were added to the magnetically stirred isocyanate under an argon atmosphere and at room temperature (about 20° C. except for sample 1 which was at 43° C.) and the temperatures of the mixtures observed. The parts of catalyst are stated in terms of the solids content excluding the solvent. Stirring was continued at least until the exotherm noted began to recede. The maximum exotherms were reached in 1, 2, and 4 minutes respectively for the three preparations. All of the products were homogeneous yellow to red mobile liquids and their measured isocyanate equivalent weights are set forth in Table III.

In sample 3 after the liquid product was cooled to 25° C., 0.5 ml. of a 1:1 by weight blend of dipropylene glycol/tripropylene glycol was added. The mixture was cooled to room temperature to provide the red liquid product.

TABLE III

| Sample | 1 | 2 | 3 |
|---|---|---|---|
| Ingredients: | | | |
| Polyisocyanate I[1] | 1 eq. | — | — |
| Polyisocyanate II[2] | — | 1 eq. | 1 eq. |
| Catalyst I[3] | 0.75 pt. | — | — |
| Catalyst II[4] | — | 0.5 pt. | 0.92 pt.[5] |
| Isocyanate E.W. | 149 | 160 | 180.3 |
| Exotherm (°C.) | 74 | 70 | 71 |
| Observations | yellow liquid | yellow liquid | red liquid |

Footnotes to Table III
[1]Polyisocyanate I: A methylenebis(phenylisocyanate) mixture comprising about 28 percent o,p'-MDI and the remainder of the mixture comprising about 72 percent p,p'-MDI; I.E. = about 125.
[2]Polyisocyanate II: A methylenebis(phenylisocyanate) mixture comprising about 50 percent o,p'-MDI and the remainder of the mixture comprising about 50 percent p,p'-MDI; I.E. = about 125.
[3]Catalyst I: The catalyst composition described in Example 3 above.
[4]Catalyst II: The catalyst composition described in Example 4 above.
[5]Catalyst II: The same catalyst composition described in Example 4 but prepared and employed as an 8 percent by weight solution in dimethyl sulfoxide.

EXAMPLE 19

This example sets forth a series of six isocyanurate-modified polyisocyanates (samples 4 through 9, inclusive) all based on the 50 percent o,p'-MDI designated Polyisocyanate II above. The same catalyst was used throughout the series but in the varying proportions in parts by weight (excluding solvent weight) set forth in Table IV.

The same procedure described in the previous example was employed with the isocyanate being at about 20° C. in each case. The exception was sample 7. In sample 7, the catalyst was added in two portions, first at 0.75 part wherein the maximum exotherm rose to 48° C. in 4 minutes, the sample allowed to cool to 23° C. and the second 0.75 part added resulting in the 63° C. exotherm in a 3 minute period.

The efficiency of each preparation was calculated in terms of the equivalents of isocyanate consumed per catalyst equivalent. These values are shown in Table IV.

A comparison of the data set forth in Table IV shows clearly how an increase in catalyst concentration results in a higher exotherm which gives rise to a corresponding decrease in efficiency in terms of isocyanate consumed per equivalent of catalyst used. More importantly, sample 7 demonstrates how catalyst deactivation can be controlled thereby controlling the levels of isocyanurate produced. Comparing sample 6 with 7, it will be noted that using the same proportion of catalyst in both, sample 7 has a higher I.E. with lower exotherm and greater catalyst efficiency compared to sample 6.

TABLE IV

| Sample | 4 | 5 | 6 | 7 | 8 | 9 |
|---|---|---|---|---|---|---|
| Ingredients: | | | | | | |

TABLE IV-continued

| Sample | 4 | 5 | 6 | 7 | 8 | 9 |
|---|---|---|---|---|---|---|
| Polyisocyanate II[1] | 1 eq. | 1 eq. | 1 eq. | 1 eq. | 1 eq. | 1 eq. |
| Catalyst I[2] | 0.4 | 0.75 | 1.5 | 0.75 0.75 | 2.25 | 3.0 |
| Exotherm (°C.) | 29 | 52 | 79 | 48 63 | 90 | 95 |
| Time to reach exotherm (in minutes) | 16.5 | 4 | 2 | 4 3 | 1 | 45 secs. |
| Eq. of NCO consumed per catalyst eq. | 96 | 74 | 61 | 75 | 48 | 39 |
| Isocyanate E.W. | 139 | 148 | 168 | 182 | 180 | 187 |
| Viscosity (cps at 25° C.) | 70 | 200 | 4400 | — | 19,200 | 24,000 |

Footnotes to Table IV
[1]Polyisocyanate II: The same 50% o,p'-MDI described in footnote 2 of Table III above; I.E. = 125; visc. (cps at 25° C.) = 35.
[2]Catalyst I: The same catalyst composition described in Example 3 above.

EXAMPLE 20

This example sets forth a flexible polyurethane foam prepared with an isocyanurate-modified polyisocyanate in accordance with the present invention using the ingredients in the proportions of parts by weight set forth in Table V.

The Polyisocyanate III was an isocyanurate-modified polyisocyanate prepared from a 50 percent o,p'-MDI similarly to sample 2 above. All of the ingredients except the polyisocyanate were mixed in a plastic cup using a drill press motor equipped with a stirring paddle. The Polyisocyanate III was added and the mixture stirred vigorously for 5 seconds and then poured into a 12"×12"×4" deep covered aluminum mold and allowed to rise. The rise profile data set forth in Table V was determined on a free rise sample in a cup.

A good foam was obtained from the mold and after curing for at least 1 week at room temperature (about 20° C.) was subjected to the tests set forth in Table V. The physical properties of the foam were found to be good.

TABLE V

| Ingredients: | |
|---|---|
| Polyisocyanate III[1] | 56.65 |
| Niax 11-27[2] | 90 |
| Niax 34-28[3] | 30 |
| Water | 3 |
| Niax A-1[4] | 0.2 |
| M-UL-1[5] | 0.0025 |
| L-5309[6] | 0.1 |
| DC-5098[7] | 0.02 |
| Foam rise profile (secs.)[8] | |
| Mix | 5 |
| Initiation | 7 |
| Gel | 43 |
| Rise | 84 |
| Firm | 96 |
| Properties: | |
| Density (pcf) | 2.54 |
| Tensile str. (psi) | 14 |
| Tear str. (pli) | 2.6 |
| Elongation at break (%) | 140 |
| 75% Compression set[9] | 20.3% |
| 50% Humid age compression set[9] | 77.1% |

TABLE V-continued

| | |
|---|---|
| Ball rebound (%)[9] | 58% |

Footnotes to Table V
[1]Polyisocyanate III: An isocyanurate-modified polyisocyanate prepared from a 50% o,p'-MDI similarly to sample 2 of Example 18 and having an I.E. = 147.
[2]Niax 11-27: A polypropyleneoxypolyethyleneoxy triol, 6200 MW, supplied by Union Carbide Corp., Danbury, Conn.
[3]Niax 34-28: A 5000 MW polymer polyol with 21% styrene/acrylonitrile supplied by Union Carbide.
[4]Niax A-1: A solution of 70% bis(2-dimethylaminoethyl)-ether in dipropylene glycol supplied by Union Carbide.
[5]M-UL-1: Dibutyltin didodecyl mercaptide supplied by Witco Chemical, New York, N.Y.
[6]L-5309: A silicone surfactant for high resilience foam supplied by Union Carbide.
[7]DC-5098: A silicone glycol copolymer, visc. = 250 cps (25° C.) supplied by Dow Corning Corp., Midland, Mich.
[8]The foam rise profile was determined separately as a free rise sample in a cup.
[9]Compression set and ball rebound tests in accordance with ASTM Test Method D-3574.

EXAMPLE 21

The following example sets forth the partial trimerization of hexamethylene diisocyanate to form an isocyanurate-modified polyisocyanate in accordance with the present invention.

A 100 ml. (0.62 mole) sample of hexamethylene diisocyanate was placed in an Erlenmeyer flask equipped with magnet stirrer. Under an argon atmosphere and during stirring a 2.57 g. sample of the catalyst composition (solvent weight excluded) prepared in accordance with Example 9 above was added to the flask. The mixture exothermed to 28° C. after about 5 minutes. Stirring was continued and over a 5 hour period the orange liquid product cooled to 22° C.

Thus there was obtained an isocyanurate-modified hexamethylene diisocyanate prepolymer; I.E.=104.

EXAMPLE 22

Using the procedure set forth in Example 21, the following example sets forth the partial trimerization in accordance with the present invention of a liquefied methylenebis(phenylisocyanate) which was obtained by treating MDI in accordance with U.S. Pat. No. 3,384,653 to form a minor proportion of carbodiimide groups or the uretoneimine adducts thereof with MDI (I.E.=144).

A 1.98 g. sample of the catalyst composition in accordance with Example 17, dissolved in 10 ml. of Poly-G 55-112 was added to 250 g. of the liquid isocyanate at about 19° C. The reaction temperature rose to a maximum of 28° C. before slowly receding to room temperature. Stirring was continued for 7 hours and the mixture became more viscous but remained clear.

Thus there was obtained an isocyanurate-modified liquid MDI product, I.E.=174.1. After standing for one week the I.E. had increased to 192.0.

EXAMPLE 23

This example sets forth six trimerizations (samples 10 through 15, inclusive) in accordance with the present invention. The same liquefied methylenebis(phenylisocyanate) described in Example 22 was used in all six samples. The trimerizations were carried out using the procedure set forth in Example 21 and the proportions in parts by weight of the catalyst compositions (excluding solvent weight) in accordance with Example 15 and Example 6 above, expressed in parts by weight per equivalent of isocyanate set forth in Table VI. Starting temperatures were 20° to 25° C.

As the parts of catalyst of Example 15 were reduced successively by a factor of about one-half in each case (samples 11 and 12) the exotherm was reduced accordingly. In all three polymerizations, the solid trimer product was formed on standing overnight under ambient temperature conditions.

The catalyst of Example 6 showed much greater activity at the higher level in respect of trimerizing the isocyanate. In sample 13, the isocyanate exothermed rapidly to 132° C. upon mixing in the catalyst with solidification to trimer following in about 15 to 20 seconds. In sample 14, after the catalyst was mixed in it took approximately 30 minutes to reach 33° C. whereupon the temperature rapidly rose to 100° C. Solidification to solid polymer followed shortly thereafter.

For sample 15 it required an overnight period of standing to bring about complete polymerization to solid product.

TABLE VI

| Sample | 10 | 11 | 12 | 13 | 14 | 15 |
|---|---|---|---|---|---|---|
| Catalyst (pts./NCO eq.): | | | | | | |
| Example 15 | 0.89 | 0.36 | 0.18 | — | — | — |
| Example 6 | — | — | — | 1.35 | 0.34 | 0.17 |
| Exotherm (°C.) | 61 | 39 | 26 | 132 | 30 mins./ 33° C.; then rapidly to 100° C. | 3½ hrs./ 65° C. |
| Time to complete trimerization | standing overnight | standing overnight | standing overnight | 15–20 seconds | 15–20 seconds near the 100° C. mark | standing overnight |

EXAMPLE 24

Using the procedure set forth in Example 21, the liquefied methylenebis(phenylisocyanate) set forth in Example 22, and the various catalyst compositions set forth in Table vII expressed as parts by weight (excluding solvent weight) per equivalent of isocyanate, there were prepared eight solid polyisocyanurate samples in accordance with the present invention (samples 16 through 23, inclusive).

The starting temperatures were about 20° C. in all cases. In those cases where the exotherm is expressed just in terms of the temperature without a time being given, i.e. samples 16, 19, and 21, the temperatures were reached slowly but remained at those levels for prolonged periods (all day). However, even at such low temperatures the trimerization process continued to form the solid polymer products.

TABLE VII

| Sample | 16 | 17 | 18 | 19 | 20 | 21 | 22 | 23 |
|---|---|---|---|---|---|---|---|---|
| Catalyst (pts./NCO eq.): | | | | | | | | |
| Ex. 16 | 1.76 | | | | | | | |
| Ex. 7 | | 1.70 | | | | | | |
| Ex. 8 | | | 1.47 | | | | | |
| Ex. 10 | | | | 2.13 | | | | |
| Ex. 11 | | | | | 3.05 | | | |
| Ex. 12 | | | | | | 1.63 | | |
| Ex. 13 | | | | | | | 2.06 | |
| Ex. 14 | | | | | | | | 1.74 |
| Exotherm (°C.) | 22 | 15 min./ | 1 hr./ | 25 | 2 hrs./ | 23 | 15 min./ | 2 hrs./ |
| Time to complete trimerization | standing overnight | 1 hr. | standing overnight | standing overnight | standing overnight | standing overnight | standing overnight | standing overnight |

EXAMPLE 25

Using the procedure set forth in Example 21, 250 g. of the liquefied methylenebis(phenylisocyanate) set forth in Example 22 was trimerized in accordance with the present invention by mixing in 2.57 g. of the freshly prepared catalyst composition described in Example 9 dissolved in 10 ml. of Poly-G 55-112 (1.5 parts catalyst per equivalent of isocyanate).

In less than one minute the reaction mixture reached a maximum of 121° C. Within ten minutes the mixture was converted into a solid block of trimerized isocyanate.

The reaction was repeated using four day old catalyst. The exotherm was 122° C. and the solid polymerized to the solid state within about 5 minutes. Repetition of the reaction using three month old catalyst but at the proportion of 2.97 parts per NCO eq. resulted in gelation of the isocyanate within about 15 seconds of mixing and a maximum exotherm of 161° C. within about one minute.

EXAMPLE 26

A molded polyisocyanurate polyurethane polymer prepared in accordance with the present invention was obtained by thoroughly blending in a plastic cup 144 g. (1.0 eq.) of the liquefied methylenebis(phenylisocyanate) described in Example 22, 6 drops of dibutyltin dilaurate, 2.57 g. of the catalyst composition in accordance with Example 9 dissolved in 5 ml. of Poly-G 55-112, and 40 g. (0.08 eq.) of a polyol E-2105 (a polyoxyethylenepolyoxypropylene diol of 1000 M.W., supplied by Texaco Chemical Co., Bellaire, Tex.). The reaction mixture was stirred for 5 to 7 seconds and cast into an open unheated steel mold measuring 8" by 8" by ⅛.

After 5 minutes the orange colored polyisocyanurate-polyurethane part was removed from the mold.

What is claimed is:

1. A flexible polyisocyanurate-urethan foam prepared by the reaction of an organic polyol, a blowing agent, a urethane catalyst, and a polyisocyanate prepolymer containing isocyanurate linkages prepared by catalytically trimerizing an aromatic polyisocyanate in the presence of a composition comprising a solution of the product obtained by reacting, in an inert solvent, substantially equimolar proportions of a ketene-aminal and an olefin having the respective formulae (I) and (II)

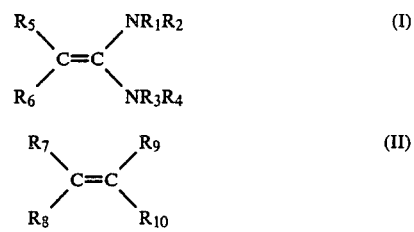

wherein $R_1$, $R_2$, $R_3$, and $R_4$ when taken separately are independently selected from the group consisting of lower-alkyl, aralkyl, cycloalkyl, and, when taken together as $R_1$ with $R_2$ and $R_3$ with $R_4$ with the respective nitrogen atoms to which they are attached represent independently heterocyclic groups having 6 or 7 ring atoms, $R_5$ and $R_6$ are independently selected from the group consisting of hydrogen, lower-alkyl, aryl, aralkyl, and cycloalkyl, $R_7$ and $R_8$ when taken separately are independently selected from the group consisting of hydrogen, lower-alkyl, aryl, aralkyl, and cycloalkyl, provided that $R_7$ and $R_8$ are not both hydrogen at the same time, and, $R_7$ and $R_8$, when taken together with the carbon atom to which they are attached represent a cyclic hydrocarbon group having 5 or 6 carbon atoms in the ring, and $R_9$ and $R_{10}$ represent the same or different electron withdrawing groups.

2. A flexible foam according to claim 1 wherein in said ketene-aminal (I) $R_5$ and $R_6$ are both hydrogen.

3. A flexible foam according to claim 1 wherein in said olefin (II) $R_7$ and $R_8$ are hydrogen and aryl respectively and $R_9$ and $R_{10}$ are both the same electron withdrawing group.

4. A flexible foam according to claim 1 wherein said aromatic polyisocyanate is a liquid methylenebis(phenylisocyanate) having a high ortho-para' isomer content.

5. A flexible foam according to claim 4 wherein said ortho-para' content is about 50 percent with the remainder being para-para' and said catalyst composition comprises a solution of the product obtained by reacting 1,1-bis(N-morpholinyl)ethylene with p-(N-morpholinyl)benzylidene malononitrile in dimethylacetamide.

* * * * *

UNITED STATES PATENT AND TRADEMARK OFFICE
CERTIFICATE OF CORRECTION

PATENT NO. : 4,719,245

DATED : January 12, 1988

INVENTOR(S) : Dale F. Regelman

It is certified that error appears in the above-identified patent and that said Letters Patent is hereby corrected as shown below:

Cover Page of Patent, ABSTRACT, fourth line from bottom "discosed" should read -- disclosed --. Column 1, line 15 "ketene-animals" should read -- kentene-aminals --; line 52 "ketene-animal" should read -- ketene aminal --. Column 2, line 38 "hexahydroxazepinyl," should read -- hexahydroazepinyl, --; line 50 "to for radicals" should read -- to form radicals --. Column 3, in the formulae IV and V, lines 20 through 25 that portion of the formula which reads

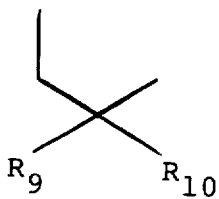   should read   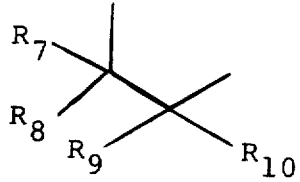

Column 4, line 58 "bis(N-piperidiny)-" should read -- bis(N-piperidinyl)- --. Column 5, line 53 "conditions" should read -- conditions. --. Column 6, line 15 "hydrogen," should read -- hydrogen: --. Column 8, line 31 "EXAMPLES 1-15" should read -- EXAMPLES 1-5 --; TABLE I, Ex. 2 "1,1-bis(N-morpholinyl)ethylene (0.00065 m)" should read -- 1,1-bis(N-morpholinyl)ethylene (0.0065 m) --; TABLE I, Ex. 2 "1,1-bisacetyl-2-phenylthylene (0.0065 m)" should read -- 1,1-bisacetyl-2-phenylethylene (0.0065 m). Column 10, TABLE II, Ex. 7 "diethyl benzylidene malonate" should read -- diethyl benzylidene malonate (0.0065 m) --; TABLE II, Ex. 8 "diethyl ethylidene malonate" should read -- diethyl ethylidene-malonate (0.0065 m) --; TABLE II,

UNITED STATES PATENT AND TRADEMARK OFFICE
CERTIFICATE OF CORRECTION

PATENT NO. : 4,719,245

DATED : January 12, 1988

INVENTOR(S) : Dale F. Regelman

It is certified that error appears in the above-identified patent and that said Letters Patent is hereby corrected as shown below:

Ex. 17  "1,1-bis(dimethylamino)-2-methylethylene (0.0065 m)" should read -- 1,1-bis(dimethylamino)-2,2-dimethylethylene (0.0065 m) --. Column 14, line 56 "Table vII" should read -- Table VII --. Columns 15 and 16, TABLE VII at Exotherm (°C) under column 17 "15 min./" should read -- 15 min./83°C --; under column 18 "1 hr./" should read -- 1 hr./40°C --; under column 20 "2 hrs./" should read -- 2 hrs./35°C --; under column 22 "15 min./" should read -- 15 min./26°C --; under column 23 "2 hrs./" should read -- 2 hrs./43°C --. Column 15, line 53 "1/8" should read -- 1/8" --; Claim 1, line 57 "polyisocyanurate-urethan" should read -- polyisocyanurate-urethane --.

Signed and Sealed this

Eleventh Day of October, 1988

Attest:

DONALD J. QUIGG

Attesting Officer

Commissioner of Patents and Trademarks